(12) United States Patent
Petrov et al.

(10) Patent No.: US 7,067,807 B2
(45) Date of Patent: Jun. 27, 2006

(54) CHARGED PARTICLE BEAM COLUMN AND METHOD OF ITS OPERATION

(75) Inventors: Igor Petrov, Holon (IL); Pavel Adamec, Haar (DE); Zvika Rosenberg, Mevasseret Zion (IL)

(73) Assignee: Applied Materials, Israel, Ltd., Rehovot (IL)

( * ) Notice: Subject to any disclaimer, the term of this patent is extended or adjusted under 35 U.S.C. 154(b) by 0 days.

(21) Appl. No.: 10/937,802

(22) Filed: Sep. 8, 2004

(65) Prior Publication Data

US 2006/0049348 A1 Mar. 9, 2006

(51) Int. Cl.
*H01J 37/28* (2006.01)
*H01J 37/145* (2006.01)

(52) U.S. Cl. ............... 250/307; 250/306; 250/309; 250/310; 250/311; 250/398; 250/440.11

(58) Field of Classification Search ............... None
See application file for complete search history.

(56) References Cited

U.S. PATENT DOCUMENTS

| | | | | |
|---|---|---|---|---|
| 4,943,722 A * | 7/1990 | Breton et al. | ............... | 250/310 |
| 5,789,748 A * | 8/1998 | Liu et al. | ............... | 250/310 |
| 6,069,363 A * | 5/2000 | Golladay | ............... | 250/396 R |
| 6,344,750 B1 * | 2/2002 | Lo et al. | ............... | 324/751 |
| 6,472,662 B1 * | 10/2002 | Archie | ............... | 250/307 |
| 6,559,459 B1 * | 5/2003 | Tanaka et al. | ............... | 250/491.1 |
| 6,566,897 B1 * | 5/2003 | Lo et al. | ............... | 324/751 |
| 6,721,052 B1 * | 4/2004 | Zhao et al. | ............... | 356/369 |
| 6,797,953 B1 * | 9/2004 | Gerlach et al. | ............... | 250/310 |
| 6,842,251 B1 * | 1/2005 | Holden | ............... | 356/445 |
| 6,897,442 B1 * | 5/2005 | Petrov | ............... | 250/310 |
| 2002/0033449 A1 * | 3/2002 | Nakasuji et al. | ............... | 250/306 |
| 2002/0117967 A1 * | 8/2002 | Gerlach et al. | ............... | 315/13.1 |
| 2002/0148961 A1 * | 10/2002 | Nakasuji et al. | ............... | 250/311 |
| 2003/0132382 A1 * | 7/2003 | Sogard | ............... | 250/311 |
| 2004/0173746 A1 * | 9/2004 | Petrov et al. | ............... | 250/310 |
| 2004/0211913 A1 * | 10/2004 | Petrov | ............... | 250/396 R |
| 2005/0045821 A1 * | 3/2005 | Noji et al. | ............... | 250/311 |
| 2006/0016988 A1 * | 1/2006 | Petrov et al. | ............... | 250/310 |

* cited by examiner

*Primary Examiner*—John R. Lee
*Assistant Examiner*—Bernard E. Souw
(74) *Attorney, Agent, or Firm*—Patterson & Sheridan LLP

(57) ABSTRACT

A method and system are presented for controlling inspection of a sample with a charged particle beam. A certain given voltage is supplied to an anode of the column to provide a required accelerating voltage for a charged particle beam. A certain negative voltage is supplied to the sample selected so as to provide a desirably high effective voltage of the column at said given voltage of the anode. A certain voltage is supplied an electrode of a lens arrangement located closer to the sample, this voltage being selected to satisfy one of the following conditions: the electrode voltage is either equal to or slightly lower than that of the sample; and the electrode voltage is significantly higher than that of the sample.

33 Claims, 7 Drawing Sheets

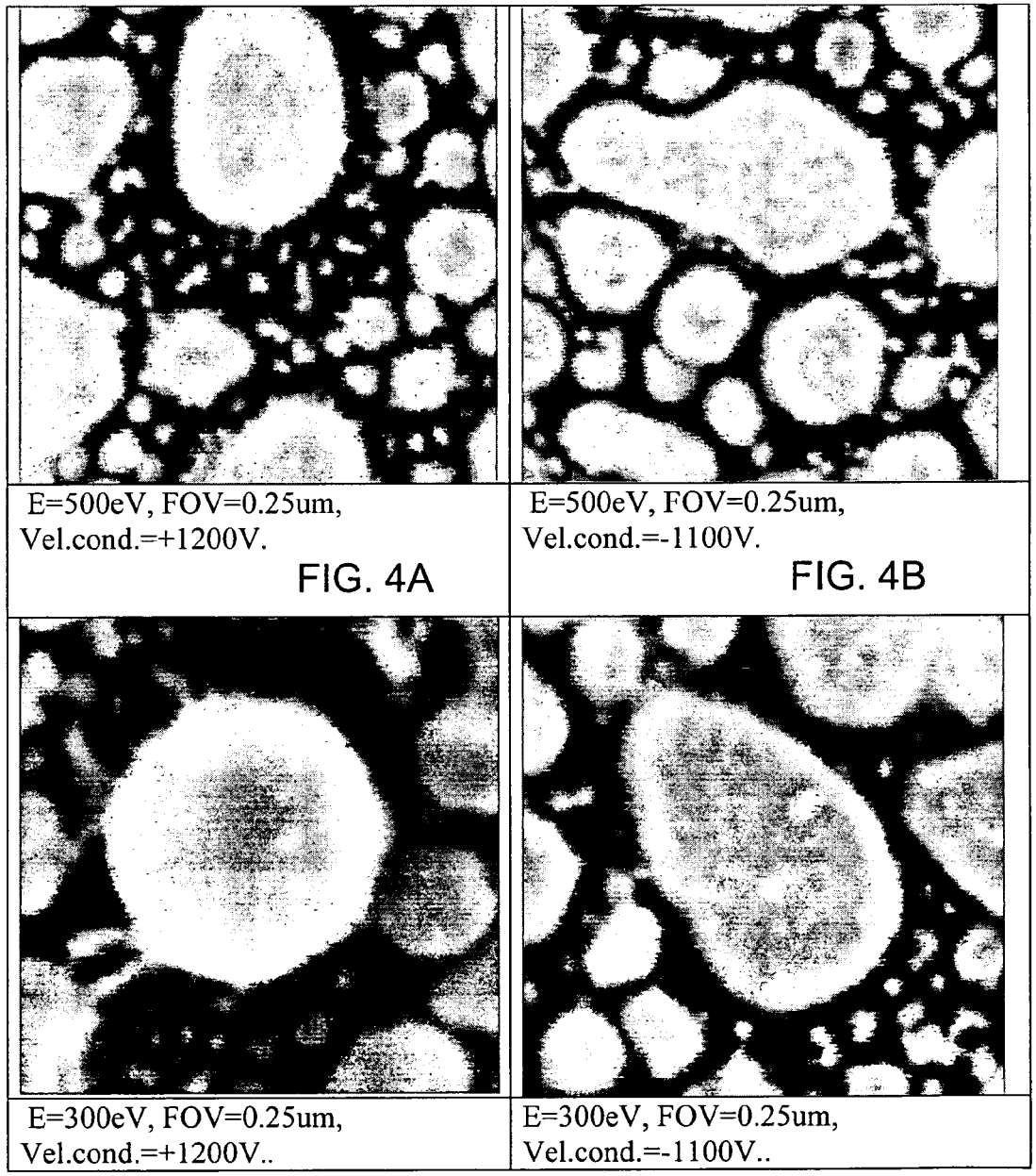

HAR mode
8kV, Vcap=3kV, Vwafer=0V.   12kV (Vcol=9kV, Vcap=0V, Vwafer=-3kV)
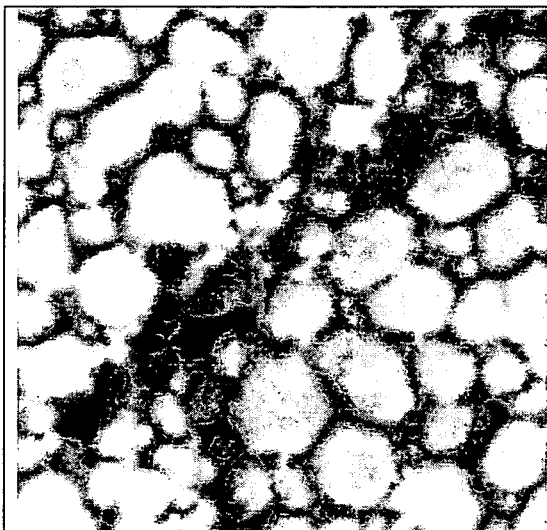
E=200eV, FOV=0.5um, Vel.cond.=+1200V.
FIG. 5A
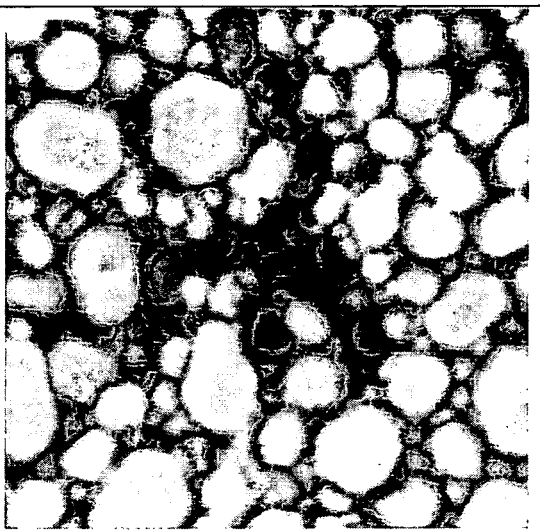
E=200eV, FOV=0.5um, Vel.cond.=-1100V.
FIG. 5B
. E=200eV, FOV=0.25um, Vel.cond.=+1200V..
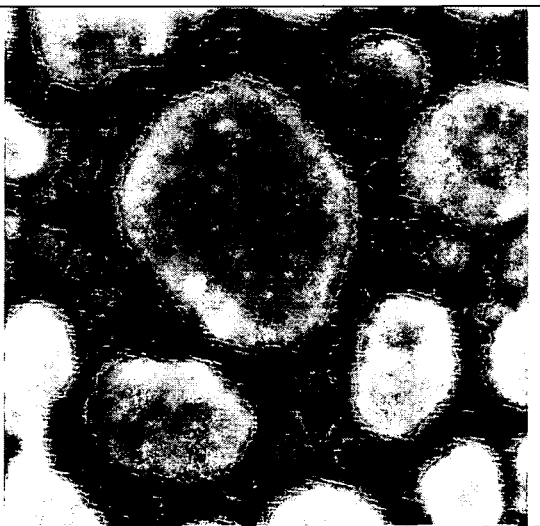
. E=200eV, FOV=0.25um, Vel.cond.=-1100V..
FIG. 5C              FIG. 5D

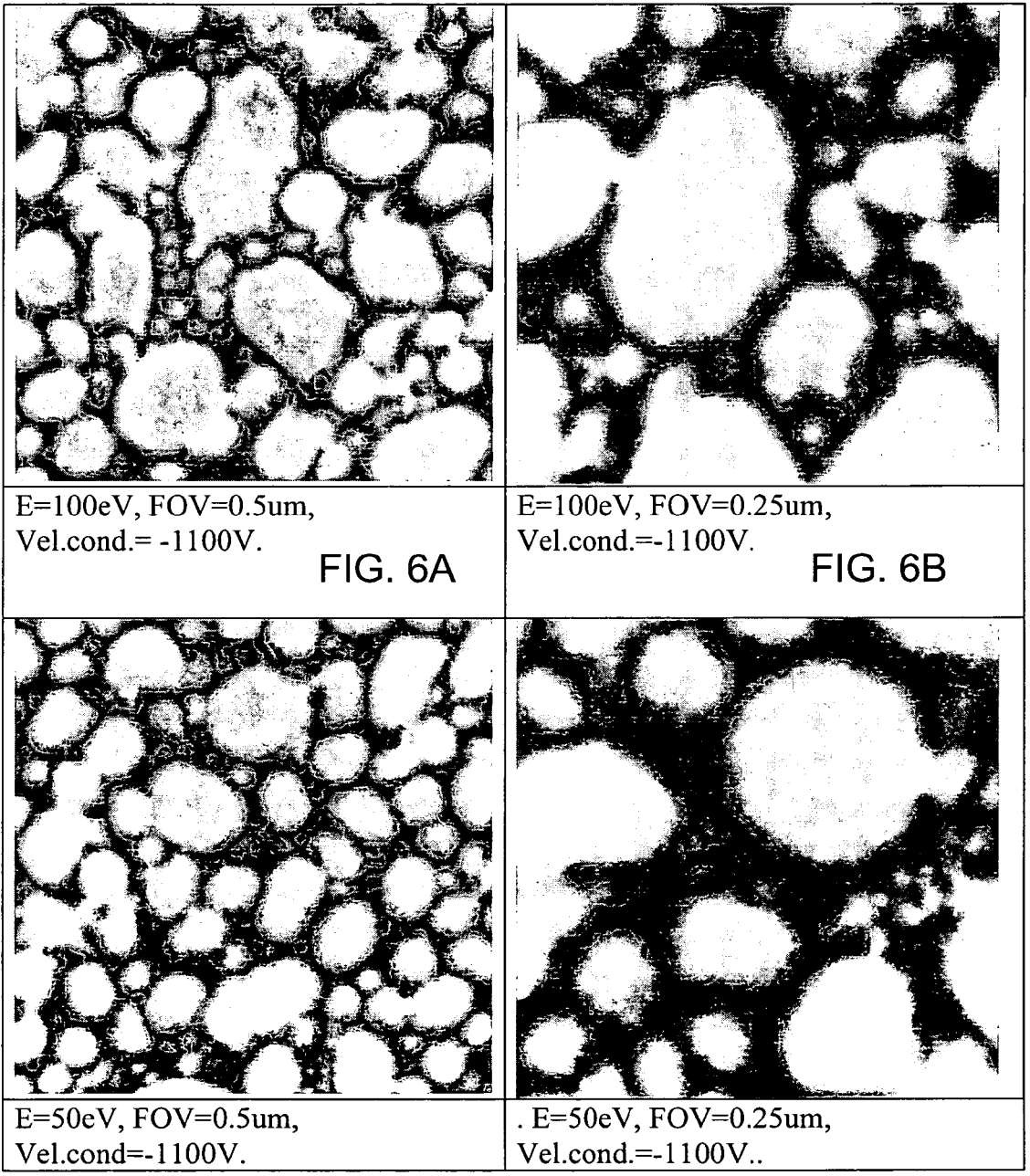

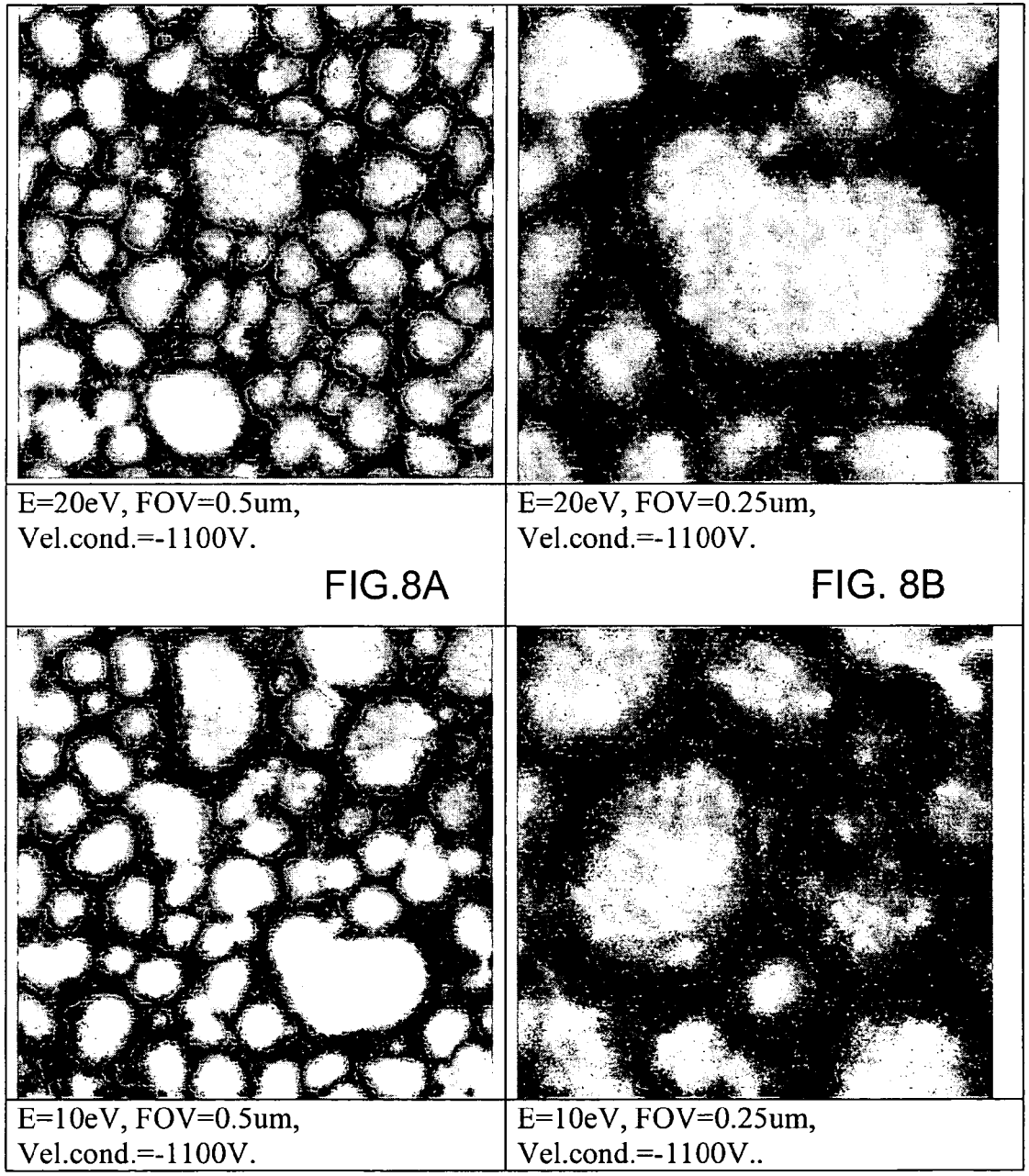

CHARGED PARTICLE BEAM COLUMN AND METHOD OF ITS OPERATION

FIELD OF THE INVENTION

The present invention relates to a charged particle beam column and a method of its operation.

BACKGROUND OF THE INVENTION

Charged particle beam columns are typically employed in scanning electron microscopy (SEM), which is a known technique widely used in the manufacture of semiconductor wafers, being utilized in a CD metrology tool, the so-called CD-SEM (critical dimension scanning electron microscope), and a defect review SEM. In a SEM, the region of a sample to be examined is two-dimensionally scanned by means of a focused primary beam of electrically charged particles, usually electrons. Irradiation of the sample with the primary electron beam releases secondary (and/or backscattered) electrons. The secondary electrons are released at that side of the sample at which the primary electron beam is incident, and move back to be captured by a detector, which generates an output electric signal proportional to the so-detected electric current. The energy and/or the energy distribution of the secondary electrons is indicative of the nature and composition of the sample.

SEM typically includes such main constructional parts as an electron beam source (formed with a small tip called "electron gun"), an electron beam column, and a detector unit. The detection unit may be located outside the path of the primary beam propagation through the column, or may be located in the path of the primary beam (the so-called "in-column" or "in-lens" detector). The electron beam column includes inter alia a beam focusing and collecting arrangement formed by a lens arrangement and a deflector. The deflection of the primary beam provides for scanning the beam within a scan area on the sample, and also for adjusting incidence of the primary beam onto the sample (an angle of incidence and/or beam shift).

One of the common goals of all imaging systems consists of increasing the image resolution. In SEM, in order to reduce the "spot" size of the electron beam up to nanometers, a highly accelerated electron beam is typically produced using accelerating voltages of several tens of kilovolts and more. Specifically, the electron optic elements are more effective (i.e. produce smaller aberrations) when the electrons are accelerated to high kinetic energy. However, in order to avoid damaging a sample (resist structure and integrated circuit) that might be caused by such a highly energized electron beam, the electron beam is decelerated just prior to impinging onto the specimen. Deceleration of the electrons can generally be accomplished by selectively creating a potential difference between the pole piece of a magnetic objective lens and the specimen. Alternatively, the same effect can be achieved by actually introducing electrodes having selective potential applied thereto.

Another known problem of the inspection systems of the kind specified is associated with locating defects (foreign particles) on patterned surfaces. The pattern is typically in the form of a plurality of spaced-apart grooves. To detect the existence of a foreign particle located inside a narrow groove, it is desirable to tilt the scanning beam with respect to the surface, which tilting should be applied to selective locations on the specimen. A tilt mechanism may be achieved by mechanically tilting the sample holder relative to the charged particle beam column, and/or by electronically tilting the primary beam propagation axis.

SUMMARY OF THE INVENTION

There is a need in the art to improve the image resolution obtainable with a charged particle beam column by providing a novel charged particle beam column and a method of its operation.

The present invention provides for improving the image resolution by increasing the effective voltage of a charged particle beam column, namely, a voltage defined by the voltages on the anode and the sample (absolute value of a difference between the sample and anode voltages), while maintaining actual anode voltage so as to on the one hand meet a requirement for an accelerating voltage in the column and on the other hand prevent break-down in the system operation. This is implemented by appropriately distributing the voltage supply between the electrodes of the column, namely, anode-electrode, the electrode of a lens arrangement located closer to a sample under inspection, and the sample itself. The voltage supply distribution is based on supplying a certain negative voltage to the sample under inspection, and supplying to the other electrodes of the column voltages providing for a desired accelerating voltage for primary and secondary beams and a desired primary beam energy landing. The voltage supply distribution is adjusted in accordance with a required operational mode of the column, namely, normal mode or tilt mode; high-gradient electric field or fast electrons in the vicinity of the sample (High Angle Ratio or HAR mode) or low-gradient field (non-HAR mode).

The term "inspection" used herein actually signifies any monitoring of a sample by imaging it with a charged particle beam. The term "primary beam" or "primary charged particle beam" signifies a charged particle beam, which is formed by charged particles generated by a source (cathode), and which is to be directed to a sample to knock out charged particles forming a "secondary beam" (also referred to as "secondary charged particle beam"), which is to be detected. The term "normal mode" signifies the primary beam incidence onto the sample with substantially zero incident angle, i.e., substantially perpendicular to the sample's surface. The term "tilt mode" signifies the primary beam incidence onto the sample along an axis forming a certain non-zero angle with the sample's surface.

The present invention is particularly useful with a column utilizing an objective lens arrangement in the form of a combination of a magnetic objective lens and an electrostatic lens, the so-called "compound magnetic-electrostatic lens". The magnetic lens is formed by two pole pieces defining a magnetic lens gap therebetween, and the electrostatic lens is formed by three electrodes: the first electrode defined by the lower end of an anode tube, the second electrode defined by the sample's surface, and the third electrode (called "cap" electrode) located between the first and second electrodes and serving for regulating an electric field created within the vicinity of the sample.

The appropriate voltage supply distribution consists of supplying a certain negative voltage to the sample, and supplying to the electrode closest to the sample (cap electrode) either a slightly lower or substantially equal voltage to that of the sample when operation with the non-HAR mode is required, or a significantly higher voltage as compared to that of the sample when operating with the HAR mode and/or with a large electronic tilt mode (about 15 degrees).

In the conventionally used column with the "compound magnetic-electrostatic lens", the voltage distribution is typically as follows: the sample is grounded ($V_s=0$), column voltage $V_{col}$ (voltage of the anode tube) is 8 kV, cap voltage $V_{cap}$ ranges between 0 and −300V for non-HAR mode and is about 3 kV for HAR mode. With this conventional voltage distribution, when operating with normal incidence of a primary beam the resolution is limited by chromatic aberrations of the objective lens, and when operating with the tilt mode (especially large tilt mode) the resolution is limited by coma aberration; the CD precision measurement is limited by an insufficiently small spot size; the signal from detector (scintillator) especially at very low beam energy (lower than 200 eV) is limited by insufficient detector efficiency.

The appropriate voltage supply distribution of the present invention provides for significantly reducing aberrations and thus improving the efficiency of detection and the image resolution, even for a low energy primary beam, i.e., beam energy of 500 eV and lower, for both normal incidence beam mode and large electron tilt mode, and for both HAR mode and "non-HAR" mode. The inventors have shown a 14% improvement of image resolution for non-HAR mode and a 17% improvement for HAR mode when operating with a 500 eV landing energy of the primary beam. Moreover, sufficient image resolution has been obtained with the technique of the present invention for the primary beam energy landing lower than 200 eV (for beam energies of 100 eV, 50 eV and 20 eV), while the conventional technique does not provide for obtaining informative image with such low beam energies.

The charged particle beam may be an electron beam or a focused ion beam (FIB). The present invention may be used in an SEM or the like tool applied to a specimen, e.g., a semiconductor wafer, for imaging, measurements, metrology, inspection, defect review or the like purposes. For example, the present invention may be used for CD measurements, line profile measurements, copper-interconnects inspection/measurements typically performed after a photolithography process, automatic defect classification, etc.

Thus, according to one aspect of the present invention, there is provided a method of controlling inspection of a sample with a charged particle beam column, the method comprising: supplying a certain negative voltage to the sample and providing an appropriate voltage supply distribution to electrodes of the charged particle beam column to increase an effective voltage of the column, while maintaining a required accelerating voltage for a charged particle beam, the method thereby providing for improvement of image resolution of the column.

According to another aspect of the invention, there is provided a method of controlling inspection of a sample with a charged particle beam column, which utilizes an objective lens, and an electrostatic lens formed by an anode, a sample under inspection and an additional electrode located between the objective lens and the sample, the method comprising: providing an appropriate voltage supply distribution to the anode, the sample and said additional electrode to thereby increase an effective voltage of the column and allow for imaging the sample with a primary charged particle beam energy landing substantially not exceeding 300 eV.

According to yet another aspect of the invention, there is provided a method of controlling inspection of a sample with a charged particle beam column to increase image resolution of the column, the method comprising: supplying a certain negative voltage to the sample; and supplying to an electrode of the lens arrangement closer to the sample a voltage that is either slightly lower or substantially equal to that of the sample, or is significantly higher than that of the sample.

According to yet another aspect of the invention, there is provided a method of controlling inspection of a sample with a charged particle beam column to increase image resolution of the column, the method comprising supplying a certain negative voltage to a sample under inspection; and supplying to an electrode of a lens arrangement of the column closer to the sample a voltage that is either slightly lower or substantially equal to that of the sample thereby providing the column operation with a relatively low gradient electric field in the vicinity of the sample, or is significantly higher than that of the sample to thereby provide the column operation with a relatively high-gradient electric field in the vicinity of the sample.

According to yet another aspect of the invention, there is provided a method of controlling inspection of a sample with a charged particle beam column, which utilizes an objective lens, and an electrostatic lens formed by an anode, a sample under inspection and an additional electrode located between the objective lens and the sample, the method comprising: supplying a certain negative voltage to the sample; and supplying to said additional electrode a voltage that is either slightly lower or substantially equal to that of the sample thereby providing the column operation with a relatively low gradient electric field in the vicinity of the sample, or is significantly higher than that of the sample to thereby provide the column operation with a relatively high-gradient electric field in the vicinity of the sample, the method thereby providing for increasing the image resolution of the column.

Additionally, the present invention provides for improving the resolution in the electronic tilt mode operation by modifying a condenser arrangement. In the tilt mode, in order to reduce coma aberrations, the beam entrance angle into a final aperture should be smaller than that of the normal beam incidence mode. This may be achieved by using a single electrostatic condenser lens and switching it off when shifting from the normal incidence mode to the tilt mode. However, in order to prevent an insufficient electric current of the primary beam that might occur in this case, the present invention provides for using a condenser lens arrangement formed by an upper electrostatic condenser lens and a lower condenser lens that may be either electrostatic or magnetic.

Thus, according to yet another aspect of the invention, there is provided a method for operating a charged particle beam column to provide selective operation of the column in a first mode of normal incidence of a primary charged particle beam onto a sample under inspection and a second mode of the primary beam incidence onto the sample with a certain non-zero angle of incidence, the method comprising passing the primary charged particle beam, while propagating towards a focusing lens arrangement, though a condenser arrangement including first and second condensers accommodated in a spaced-apart relationship along the primary beam path; and controlling the operation of the lower condenser to reduce a numerical aperture of the beam propagation while shifting the column from the first mode to the second mode.

The present invention according to its yet another aspect provides a system for use in inspecting a sample with a charged particle beam, the system comprising a charged particle beam column including a cathode assembly, an anode tube that defines a primary beam drift space, and a focusing lens arrangement; and a voltage supply unit operable to supply a certain negative voltage to the sample and provide an appropriate voltage supply distribution to electrodes of the charged particle beam column to increase an effective voltage of the column, while providing required voltages of the cathode and anode electrodes defined by a required accelerating voltage for a charged particle beam.

According to yet another aspect of the invention, there is provided a system for use in inspecting a sample, the system comprising a charged particle beam column, a sample holder, and a voltage supply unit, the sample holder comprising upper and lower electrodes, the lower electrode being formed with an array of space-apart projections for supporting the sample by distal ends of said projections, a voltage supplied to the lower electrode defining a voltage of the sample, said upper electrode being in the form of spaced-apart electrode-elements located within the spaces between said projections, a potential difference between the upper electrode elements defining electrostatic forces flattening the sample to reduce a working distance of the column.

More specifically, the present invention is used with an SEM system for inspecting wafers, masks or reticles, and is therefore described below with respect to this application.

BRIEF DESCRIPTION OF THE DRAWINGS

In order to understand the invention and to see how it may be carried out in practice, preferred embodiments will now be described, by way of non-limiting examples only, with reference to the accompanying drawings, in which:

FIGS. 4A to 4D illustrate the experimental results comparing the image resolution of the conventional SEM system to that of the present invention, wherein FIGS. 4A and 4B show the SEM images obtained with, respectively, the conventional and inventive system, for a 500 eV primary beam energy landing, and FIGS. 4C and 4D show the SEM images obtained with, respectively, the conventional and inventive system, for a 300 eV primary beam energy landing;

FIGS. 5A to 5C illustrate the experimental results comparing the image resolution of the conventional SEM system to that of the present invention for a 200 eV primary beam energy landing, wherein FIGS. 5A and 5B show SEM images obtained with the conventional and inventive technique, respectively, at a 0.5 μm field of view, and FIGS. 5C and 5D show SEM images obtained with the conventional and inventive techniques, respectively, at a 0.25 μm field of view;

FIGS. 6A and 6B illustrate SEM images obtained with the technique of the present invention for a 100 eV primary beam energy landing and, respectively, 0.5 μm and 0.25 μm fields of view;

FIGS. 7A and 7B illustrate SEM images obtained with the technique of the present invention for a 50 eV primary beam energy landing and, respectively, 0.5 μm and 0.25 μm fields of view;

FIGS. 8A and 8B illustrate SEM images obtained with the technique of the present invention for a 20 eV primary beam energy landing and, respectively, 0.5 μm and 0.25 μm fields of view; and FIGS. 9A and 9B illustrate SEM images obtained with the technique of the present invention for a 10 eV primary beam energy landing and, respectively, 0.5 μm and 0.25 μm fields of view.

DETAILED DESCRIPTION OF THE INVENTION

Figure 1:
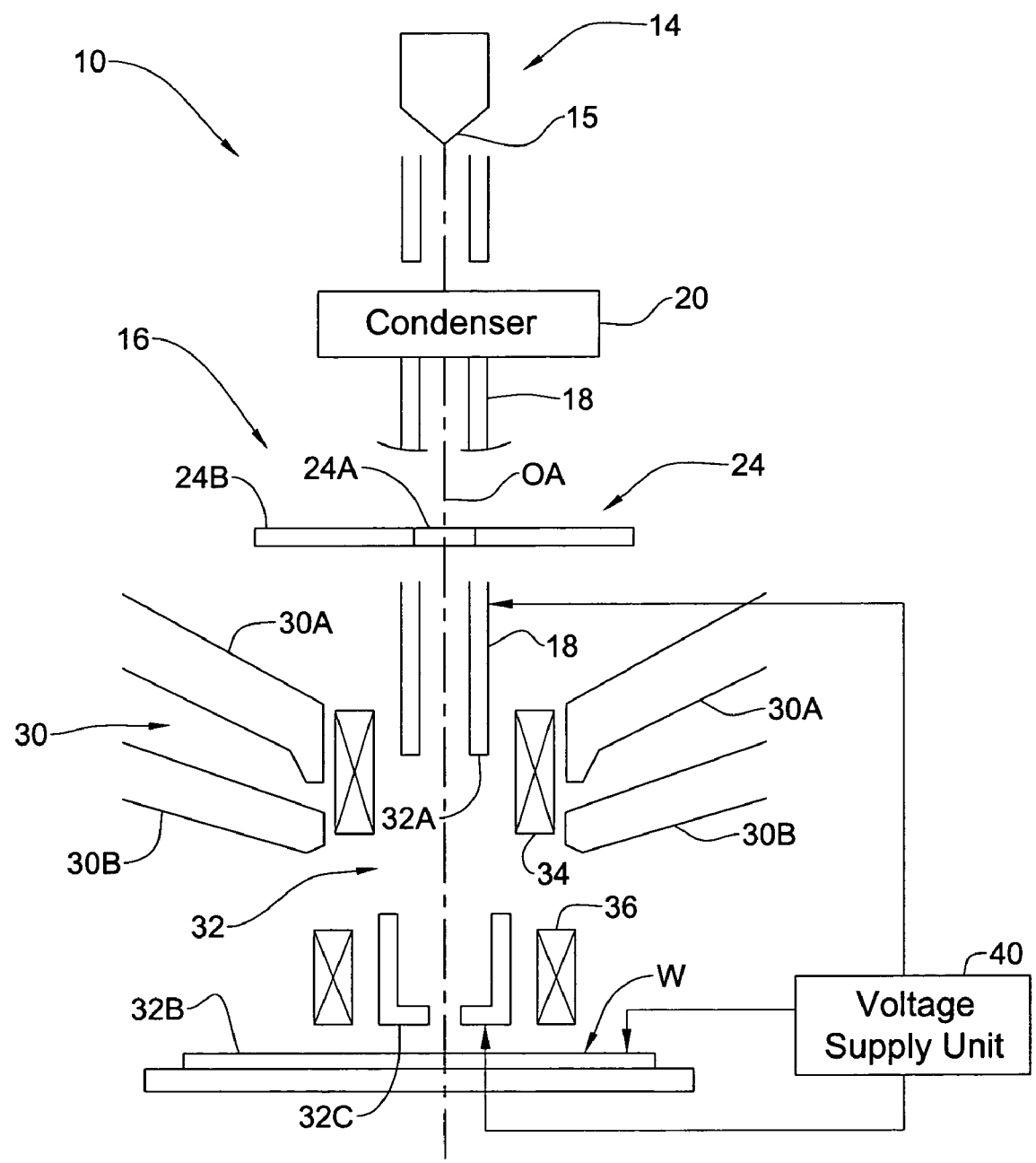
FIG. 1 schematically illustrates a charged particle beam column of the present invention.

Referrin to FIG. 1, there is schematically illustrated a SEM system 10 for inspecting/measuring a wafer W. The SEM system 10 typically comprises an electron beam source 14 (a so-called "electron gun") having a small tip (cathode) 15; a charged particle beam column 16; and a secondary electrons' detector 24. The charged particle beam column 16 includes an anode tube 18 that defines a primary beam drift space; a condenser lens arrangement 20; and a focusing arrangement 22. The longitudinal axis of the anode tube 18 defines an axis OA of the primary beam propagation towards the focusing arrangement 22. The longitudinal axis of the anode tube 18 defines an axis OA of the primary beam propagation towards the focusing arrangement 22.

In the present example, the detector 24 is the so-called "in-column detector", designed like a plate having an opening 24A surrounded by detecting regions 24B. The detector 24 is located such that the longitudinal axis of the anode tube 18 passes the opening 24A, which thus serves as a primary beam hole.

The column 16 also typically comprises beam blank means, several apertures (including a final aperture defining the primary beam diameter, and alignment coils), and a stigmator arrangement, which are not shown here.

The focusing arrangement 22 includes a lens arrangement and a deflector arrangement. The lens arrangement is a compound magnetic-electrostatic lens including a magnetic objective lens 30 and a retarding electrostatic immersion lens 32 located downstream of the lens 30 with respect to the direction of primary beam propagation. The magnetic lens 30 is formed by two pole pieces 30A and 30B defining the magnetic lens gap. The electrostatic lens 32 is formed by three electrodes: first electrode 32A constituted by the lower end of the anode tube 18, second electrode 32B constituted by the wafer's surface, and the third "cap" electrode 32C located between the electrodes 32A and 32B and serving for regulating an electric field created within the vicinity of the wafer.

The deflector arrangement is in the present example composed of two deflectors 34 and 36. The first deflector 34 is mounted within the magnetic lens gap, and the second deflector 36 is mounted within the electrostatic field produced by the lens 32. In the present example, both deflectors 18 are magnetic. It should, however, be noted that the second deflector 36 may be electrostatic (e.g. condenser plates).

Further provided in the SEM system is a voltage supply unit 40 operated to provide a desired effective voltage of the column to thereby improve the image resolution. This is achieved by appropriate distribution of the voltage supply between the anode, cap electrode 32C, and the wafer-electrode 32B.

To achieve the desired acceleration of electrons (accelerating voltage), appropriate potential difference between the cathode 15 and anode 18 should be provided. For example, the cathode voltage $V_{cathode}$ can be about $(-1)$kV and the anode voltage $V_{anode}$ can be about $(+8)$kV. Hence, the electrons are accelerated on their way towards the magnetic lens 30 having the velocities of 9 keV.

The electrostatic lens 32 acts to decelerate the electrons in the closest vicinity of the wafer W. To this end, the voltage applied to the wafer-electrode 32B is typically substantially less than that of the anode 18. In the conventional SEM utilizing the compound magnetic-electrostatic lens, the wafer is grounded ($V_w=0$), and the electrodes are biased, e.g. $V_{cathode}=(-1)$kV; $V_{anode}=(+8)$kV and $V_{cap}=(+3)$kV. Generally, in such system the image resolution may be improved by increasing the anode voltage, but this might result in a break-down in the system operation.

The landing energy of the primary electron beam is defined by a potential difference between the cathode 15 and the wafer 32B. It is known that, on the one hand, operation with a lower beam landing energy is preferred in order to prevent damaging of the sample, while, on the other hand, a sufficient image resolution is typically obtainable with a higher beam energy landing.

The present invention solves the above problem, namely, allows for high-resolution imaging with a relatively low primary beam energy landing and with a required cathode and anode voltages (to provide a desired beam acceleration and to prevent break-down in the system operation), by appropriately distributing voltages between the anode, cap-electrode and wafer-electrode to thereby obtain a desirably increased effective voltage of the column. The "effective" voltage of the column is defined by voltages of the anode and the wafer. Typically, this is the absolute value of a difference between the wafer and anode voltages. It is important to note that the present invention provides for increasing the "effective" voltage of the column, while not increasing the actual anode voltage, which is one the one hand determined by the required accelerating voltage, and on the other, is limited to prevent break-down of the system operation. The increase of the effective voltage is achieved in the present invention by supplying a certain negative voltage to the wafer-electrode 32B, and supplying to the cap electrode 32C either a slightly lower or substantially equal voltage to that of the sample when operating with a relatively low gradient field in the vicinity of the sample (non-HAR mode), or a significantly higher voltage as compared to that of the sample when operating with a high gradient field or fast electrons (HAR mode) and/or with a large electronic tilt mode.

For example, the voltage supply may be as follows: in the non-HAR mode, $V_{anode}=8$ kV, $V_{sample}=(-3)$kV and $V_{cap}=V_{cap}=(-2.9$ to $3.3)$kV or $V_{sample}=(-3)$kV, and in the HAR mode $V_{anode}=9$ kV, $V_{sample}=(-3)$kV and $V_{cap}=0$.

Potentials of the cap and the wafer electrodes are close to each other to provide a small electrostatic field between the cap and the wafer (in the non-HAR mode) and may change together from zero to −3 kV. In the HAR mode, the cap potential is more than the wafer potential to thus provide a relatively high electrostatic field between the cap and the wafer. In both non-HAR and HAR modes, increasing the negative potential improves the resolution and the detector efficiency. It should be understood that, when varying the wafer voltage and accordingly the anode voltage to provide the desired effective voltage of the column, the cathode voltage is adjusted to provide the required accelerating voltage.

Figure 2A:
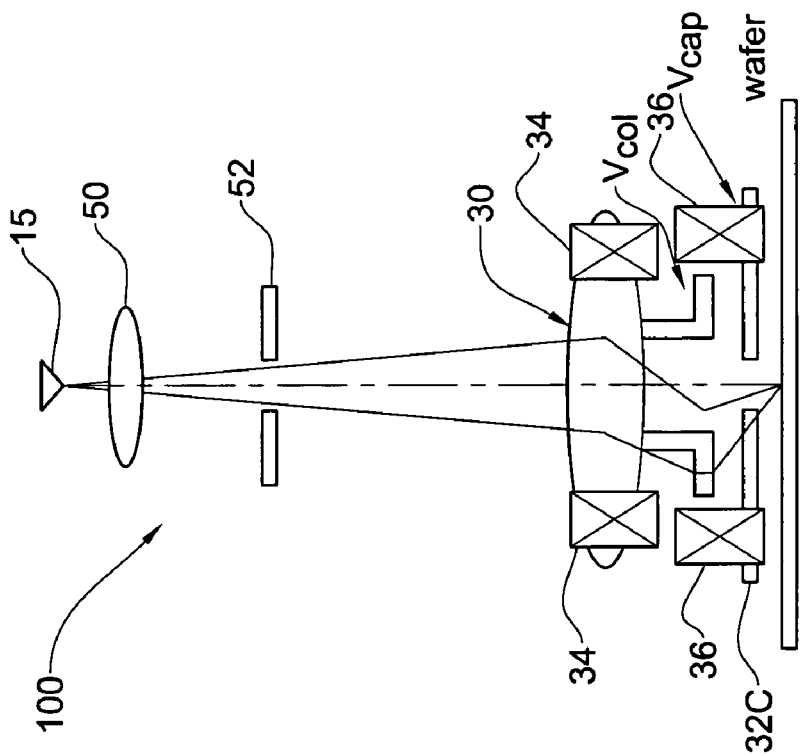
FIGS. 2A to 2C schematically illustrate the column operation with normal and tilt incidence modes.
Figure 2B:
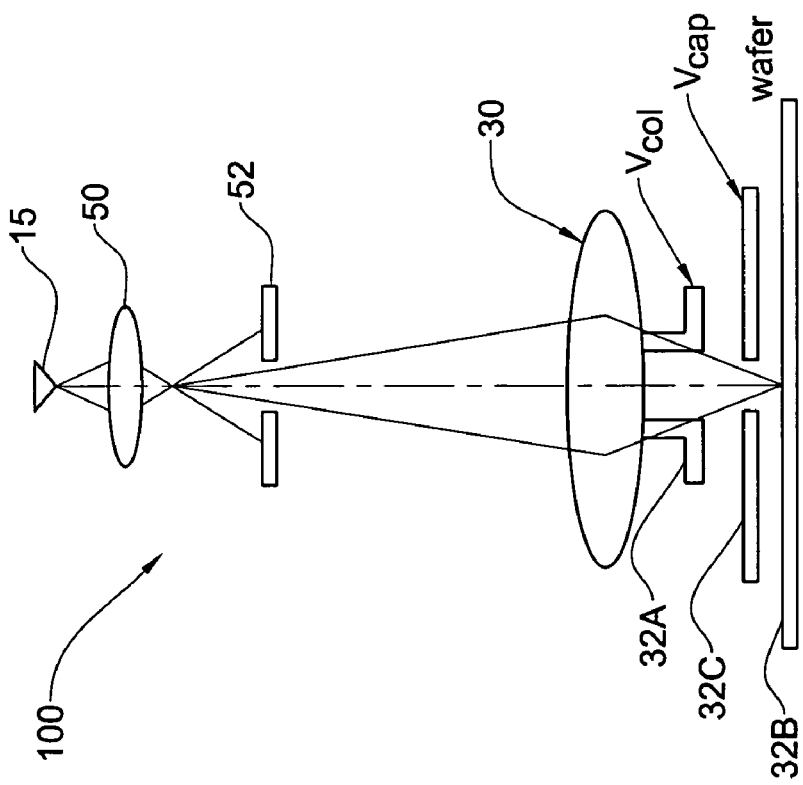

Referring to FIGS. 2A and 2B, there is schematically illustrated the operation of a SEM system 100 with, respectively, normal incidence and tilt incidence modes. To facilitate understanding, the same reference numbers are used to identify the common system components for all the examples of the invention. The system 100 includes a condenser arrangement 50 placed between a cathode tip 15 and a final aperture 52; a magnetic objective lens 30; an electrostatic retarding lens formed by electrode 32A (anode tube), wafer's surface 32B and cap electrode 32C; and deflectors 34 and 36 operable to provide the tilt on axis mode. The condenser arrangement includes a single electrostatic condenser. A voltage applied to the focusing electrode of the condenser 50 is required for the formation of the beam crossover effect before the beam enters the final aperture 52 and for providing an optimal numeric aperture to maximize the image resolution in non HAR and HAR modes. The tilt mode typically requires smaller numeric aperture angle of the beam than that of the normal incidence case. This is important for reducing coma aberration and thus improving resolution in the tilt mode. The adjustment of the numerical aperture for the normal and tilt modes may be achieved by using the single electrostatic condenser 50 and shifting it from its operative (ON) state when in the normal incidence mode to its inoperative (OFF) state for the tilt mode.

Figure 2C:
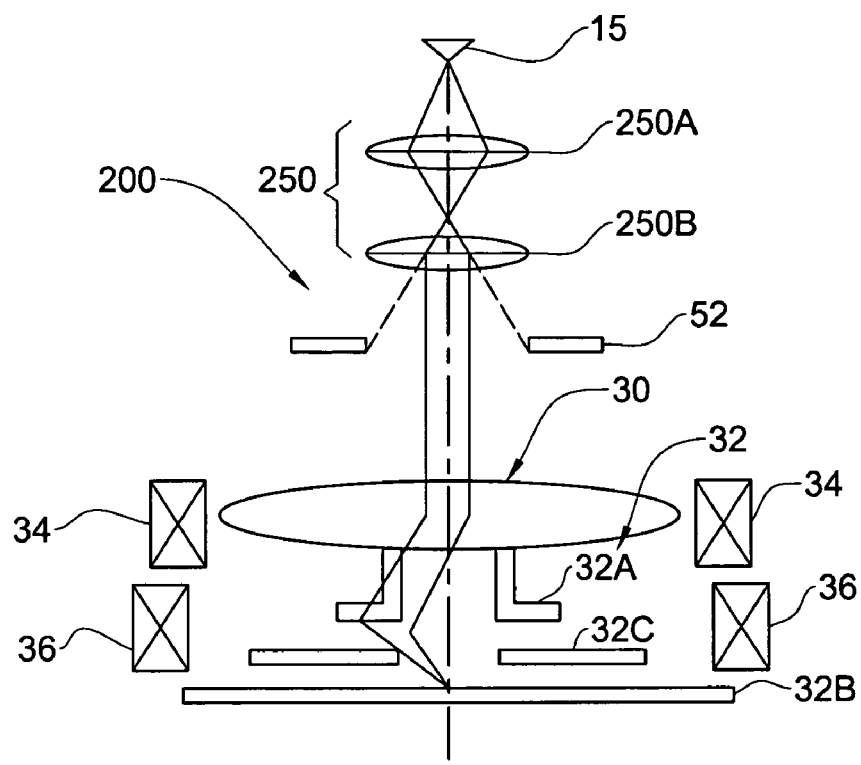

FIG. 2C illustrates a SEM system 200 according to another example of the invention. The system 200 includes a condenser arrangement 250 placed between a cathode tip 15 and a final aperture 52; a magnetic objective lens 30; an electrostatic retarding lens formed by electrode 32A (anode tube), wafers surface 32B and cap electrode 32C; and deflectors 34 and 36. Here, the condenser arrangement 250 includes a first electrostatic condenser 250A and a second condenser 250B that may be magnetic. The primary beam propagation when in the operative position of the first condenser and no second condenser (or inoperative position of the second condenser), is shown in the figure in dashed lines. As shown, the second condenser appropriately adjusts (reduces) the numerical aperture of the beam for the tilt mode.

Figure 3:
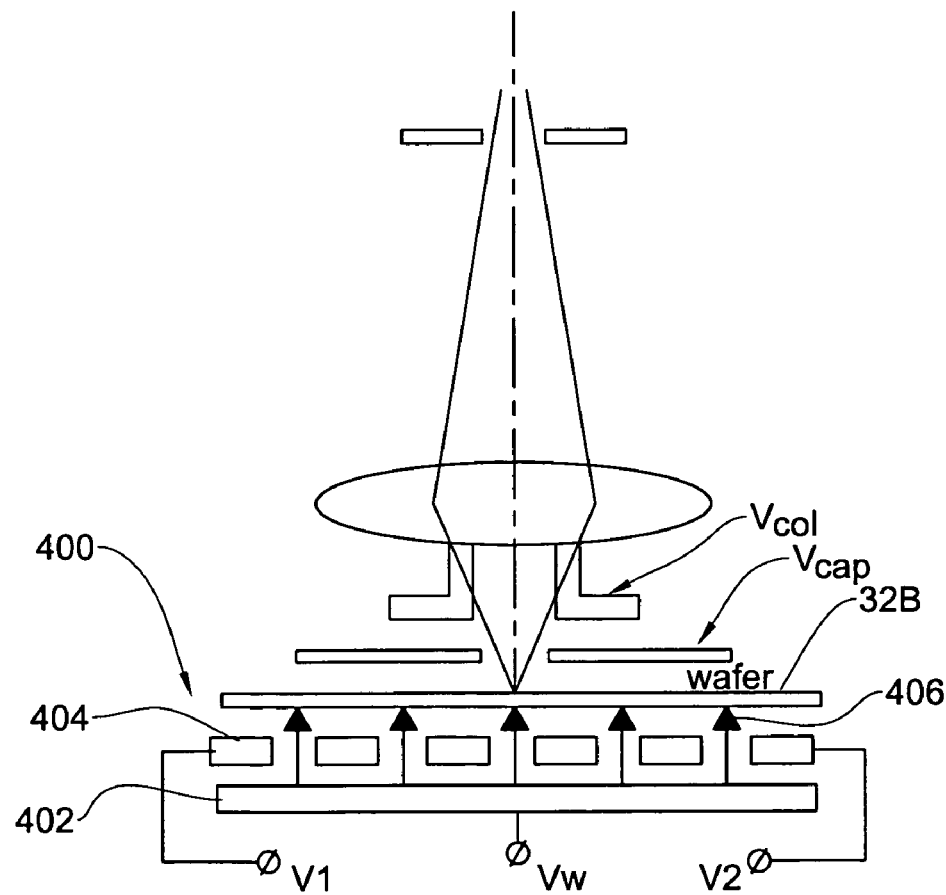
FIG. 3 illustrates a configuration of a wafer holder (chuck) according to the invention.

FIG. 3 exemplifies a wafer holder (chuck) 400 according to the invention. The chuck 400 is configured for holding a wafer by electrostatic forces. In order to minimize a working distance, which is a distance between the electrode of the lens arrangement closest to the sample's plane (cap electrode in the present example) and the sample's plane, the wafer should be flattened as much as possible. This is implemented by providing appropriate electrostatic forces. On the other hand, the voltage supply to the chuck electrodes should be such as to provide a desired negative voltage on the wafer. The chuck 400 includes a lower electrode 402 formed with an array of spaced-apart projecting pins 406 holding the wafer, and an upper electrode 404 in the form of an array of electrode elements allowing the pins passage through the spaces between the electrode elements. A voltage supplied to the lower electrode 402 defines the wafer-electrode voltage, and a potential difference applied to the upper electrode elements flattens the wafer. The chuck electrodes give a base potential of the wafer $V_w=V_{402}$ and two potentials $V_1=V_{402}+\Delta V$ and $V2=V_{base}-\Delta V$ (e.g., $\Delta 700V$). For example, $V_{402}=V_w=(-3)$kV, $V_1 2400V$ and $V_2=(-3600)$V.

The technique of the present invention (appropriate voltage supply distribution) provides for significantly improving the image resolution even when operating with the low beam energy landing. The inventors have shown that the appropriate voltage supply to the electrodes of the column provides for improving the image resolution by 14% for a 500 eV primary beam energy landing in the non-HAR mode, and by 17% for the HAR mode, as compared to the conventional situation with a grounded sample. The following are several experimental results for HAR mode operation with different primary beam landing energies.

FIGS. 4A to 4D illustrate the experimental results comparing the image resolution of the conventional SEM system to that of the present invention. In the present examples, the SEM system operated with the HAR mode. FIGS. 4A and 4C show the SEM images obtained for the beam energies of 500 eV and 300 eV, respectively, with the conventional operational mode: $V_{anode}$=8 kV, $V_{cap}$=3 kV, $V_{sample}$=0V. FIGS. 4B and 4D show the SEM images for beam energies of 500 eV and 300 eV, respectively, with the technique of the present invention: effective anode voltage $V_{effect}$=12 kV, $V_{anode}$=9 kV, $V_{cap}$=0V, $V_{sample}$=−3 kV.

FIGS. 5A to 5C illustrate the experimental results comparing the image resolution of the conventional SEM system to that of the present invention for a 200 eV primary beam energy landing. FIGS. 5A and 5C show SEM images obtained with fields of view of respectively 0.5 μm and 0.25 μm, using the conventional technique: $V_{anode}$=8 kV, $V_{cap}$=3 kV, $V_{sample}$=0V. FIGS. 5B and 5D show SEM images obtained with fields of view of respectively 0.5 μm and 0.25 μm, using the technique of the present invention: $V_{effect}$=12 kV, $V_{anode}$=9 kV, $V_{cap}$=0V, $V_{sample}$=−3 kV.

FIGS. 6A–6B, 7A–7B, 8A–8B and 9A–9B exemplify SEM images obtained with the technique of the present invention ($V_{effect}$=12 kV, $V_{anode}$=9 kV, $V_{cap}$=0V, $V_{sample}$=−3 kV) for primary beam energies lower than 200 eV, which cannot be obtained with the conventional technique. FIGS. 6A and 6B exemplify SEM images obtained for a 100 eV primary beam energy landing and, respectively, 0.5 μm and 0.25 μm fields of view. FIGS. 7A and 7B illustrate SEM images for a 50 eV primary beam energy landing and, respectively, 0.5 μm and 0.25 μm fields of view. FIGS. 8A and 8B show SEM images obtained for a 20 eV primary beam energy landing and, respectively, 0.5 μm and 0.25 μm fields of view. FIGS. 9A and 9B SEM images at 0.5 μm and 0.25 μm fields of view, respectively, for a 10 eV primary beam energy landing.

Those skilled in the art will readily appreciate that various modifications and changes can be applied to the embodiments of the invention as hereinbefore described without departing from its scope as defined in and by the appended claims.

The invention claimed is:

1. A method of controlling inspection of a sample with a charged particle beam column, the method comprising: supplying a certain given voltage to an anode of the column selected to provide a required accelerating voltage for a charged particle beam, supplying a negative voltage $V_{sample}$ to the sample selected to provide a desirably high effective voltage of the column at said given voltage on the anode, and supplying a certain voltage $V_{cap}$ to an electrode of a lens arrangement located closer to the sample than an objective lens of the lens arrangement, said certain voltage $V_{cap}$ being selected to satisfy one of the following conditions: $V_{cap}$ slightly lower or substantially equal to $V_{sample}$ thereby enabling operation with a relatively low-gradient electric field in the vicinity of the sample, and $V_{cap}$ is significantly higher than $V_{sample}$ thereby enabling operation with a relatively high gradient field in the vicinity of the sample.

2. The method of claim 1, wherein an absolute value of the negative voltage supplied to the sample substantially does not exceed 3 kV.

3. The method of claim 1, wherein said electrode is part of an electrostatic lens of said lens arrangement.

4. The method of claim 1, wherein the voltage supplied to said electrode of the lens arrangement is slightly lower or substantially equal to that of the sample, the column being operable with a normal incidence of a primary charged particle beam onto the sample.

5. The method of claim 1, wherein the voltage supplied to said electrode of the lens arrangement is significantly higher than that of the sample, the column being operable a primary charged particle beam impinging onto the sample with a certain non-zero angle of incidence.

6. The method of claim 5, wherein the beam incident angle is of about 15 degrees.

7. The method of claim 1, wherein the effective voltage of the column is about 11–12 kV with the charged particle beam accelerating voltage of about 9 kV.

8. The method of claim 7, wherein the anode voltage is $V_{anode}$=8 kV, the sample voltage is $V_{sample}$=(−3) kV and said electrode voltage is $V_{cap}$=(−2.9 to 3.3) kV.

9. The method of claim 7, wherein the anode voltage is $V_{anode}$=8 kV, the sample voltage is $V_{sample}$=(−3) kV and said electrode voltage is $V_{cap}$(−3) kV.

10. The method of claim 1, wherein the effective voltage of the column is about 11–12 kV, with the charged particle beam accelerating voltage of about 10 kV.

11. The method of claim 10, wherein the anode voltage is $V_{anode}$=9 kV, the sample voltage is $V_{sample}$=(−3) kV and said electrode voltage is $V_{cap}$=0.

12. The method of claim 1, wherein the voltage supplied to said electrode of the lens arrangement is slightly lower or substantially equal to that of the sample, the column operation with a 500 eV primary beam energy landing providing for the 14% image resolution improvement, as compared to operation with the grounded sample.

13. The method of claim 1, wherein the voltage supplied to said electrode of the lens arrangement is significantly higher than that of the sample, the column operation with a 500 eV primary beam energy landing providing for the 17% image resolution improvement, as compared to operation with the grounded sample.

14. The method of claim 1, providing for imaging the sample with a low primary beam energy landing.

15. The method of claim 14, wherein the primary beam energy landing substantially does not exceed 500 eV.

16. The method of claim 14, wherein the primary beam energy landing is less than 500 eV.

17. The method of claim 14, wherein the primary beam energy landing is about 10–500 eV.

18. The method of claim 1, comprising controlling a primary beam propagation towards the lens arrangement to allow for shifting the column operation between a first operational mode when the primary beam normally impinges onto the sample, and a second operational mode when the primary beam impinges onto the sample with a certain non-zero angle of incidence.

19. The method of claim 18, wherein said controlling comprises passing the primary beam through a condenser arrangement including first and second condensers accommodated in a spaced-apart relationship along an optical axis of the column, controlling the operation of the lower condenser allowing for said shifting of the column operational mode.

20. The method of claim 19, wherein the operation of the lower condenser reduces a numerical aperture of the beam propagation towards the lens arrangement.

21. The method of claim 1, wherein said certain negative voltage supply to the sample is provided by applying said certain negative voltage to a sample supporting electrode of a sample holder.

22. The method of claim 1, comprising flattening the sample while on a sample holder to thereby minimize a working distance of the column.

23. The method of claim 22, wherein said flattening is achieved by operating a sample holder to apply electrostatic forces to the sample.

24. The method of claim 23, wherein the sample holder is configured and operated to provide the desired negative voltage supply to the sample.

25. The method of claim 24, comprising holding the sample by distal ends of spaced-apart projections on a lower electrode of the sample holder, and providing an array of spaced-apart elements of an upper electrode located within the spaces between said projections, a voltage supplied to the lower electrode defining the voltage of the sample, and a potential difference between the upper electrode elements defining the electrostatic forces flattening the sample.

26. The method of claim 21, comprising holding the sample by distal ends of spaced-apart projections on a lower electrode of the sample holder, and providing an array of spaced-apart elements of an upper electrode located within the spaces between said projections, a voltage supplied to the lower electrode defining the voltage of the sample.

27. A method for operating a charged particle beam column to provide selective operation of the column in a first mode of normal incidence of a primary charged particle beam onto a sample under inspection and a second mode of the primary beam incidence onto the sample with a certain non-zero angle of incidence, the method comprising passing the primary charged particle beam, while propagating towards a focusing lens arrangement, through a condenser arrangement including first and second condensers accommodated in a spaced-apart relationship along the primary beam path; and controlling the operation of the lower condenser to reduce a numerical aperture of the beam propagation while shifting the column from the first mode to the second mode.

28. A system for use in inspecting a sample with a charged particle beam, the system comprising a charged particle beam column including a cathode assembly, an anode tube that defines a primary beam drift space, and a lens arrangement; and a voltage supply unit operable to supply a certain given to the anode to provide a desired accelerating voltage for a charged particle beam, supply a certain negative voltage $V_{sample}$ to the sample provide a desirably high effective voltage of the column at said given voltage of the anode, and supply to an electrode of the lens arrangement, closer to the sample than an objective lens of the lens arrangement, a certain voltage $V_{cap}$ selected to satisfy one of the following conditions: $V_{cap}$ slightly lower or substantially equal to $V_{sample}$ enabling operation with a relatively low-gradient electric field in the vicinity of the sample, and $V_{cap}$ is significantly higher than $V_{sample}$ enabling operation with a relatively high gradient field in the vicinity of the sample.

29. The system of claim 28, wherein the column comprises a condenser arrangement accommodated in a path of a primary charged particle beam propagating from the cathode assembly to said lens arrangement, the condenser arrangement comprising first and second condensers accommodated in a spaced-apart relationship along said path, said second lower condenser being selectively operable by the voltage supply unit to selectively reduce a numerical aperture of the beam propagation, to thereby effect shifting the column operation from a first operational mode when the primary bam normally impinges onto the sample, to a second operational mode when the primary beam impinges onto the sample with a certain non-zero angle of incidence.

30. The system of claim 29, comprising a sample holder operable by said voltage supply unit to provide flattening the sample while on the sample holder and supply the required negative voltage to the sample.

31. The system of claim 30, wherein the sample holder includes upper and lower electrodes, the lower electrode being formed with an array of space-apart projections for supporting the sample by distal ends of said projections, the voltage supplied to the lower electrode defining the voltage of the sample, said upper electrode being in the form with spaced-apart electrode-elements located within the spaces between said projections, a potential difference between the upper electrode elements defining electrostatic forces flattening the sample.

32. A charged particle beam column for inspecting a sample, the column comprising a cathode assembly, a condenser arrangement, an anode tube that defines a primary beam drift space, and a focusing lens arrangement, said condenser arrangement comprising upper and lower condensers accommodated in a spaced-apart relationship along an optical axis of the column and operable to define a required numerical aperture of a primary charged particle beam propagation towards the focusing lens arrangement, the lower condenser being selectively operable to reduce the numerical aperture to thereby selectively shift the column operation from a first mode when the primary beam normally impinges onto the sample to a second mode when the primary beam impinges onto the sample with a certain non-zero angle of incidence.

33. A sample holder for use with a charged particle beam column, the sample holder comprising upper and lower electrodes, the lower electrode being formed with an array of space-apart projections for supporting the sample by distal ends of said projections, a voltage supplied to the lower electrode defining a voltage of the sample, said upper electrode being in the form of spaced-apart electrode-elements located within the spaces between said projections, a potential difference between the upper electrode elements defining electrostatic forces flattening the sample to reduce a working distance of the column.

* * * * *

UNITED STATES PATENT AND TRADEMARK OFFICE
CERTIFICATE OF CORRECTION

PATENT NO. : 7,067,807 B2  Page 1 of 1
APPLICATION NO. : 10/937802
DATED : June 27, 2006
INVENTOR(S) : Igor Petrov et al.

It is certified that error appears in the above-identified patent and that said Letters Patent is hereby corrected as shown below:

Column 6, Line 9: Change "Referrin" to --Referring--

Column 7, Line 29: After "is", change "one" to --on--

Column 7, Line 44: After "$V_{cap}$", delete "=$V_{cap}$"

Column 7, Line 44: After "$V_{sample}$", insert -- =$V_{cap}$ --

Column 8, Line 52: Change "V2" to --$V_2$--

Column 8, Line 53: Change "$V_1$2400V" to -- $V_1$=2400V --

Column 12, Line 9: Change "bam" to --beam--

Signed and Sealed this

Twenty-first Day of November, 2006

JON W. DUDAS
*Director of the United States Patent and Trademark Office*